US011179466B2

(12) United States Patent
Kim et al.

(10) Patent No.: US 11,179,466 B2
(45) Date of Patent: Nov. 23, 2021

(54) AMPHIPHILIC BLOCK COPOLYMER COMPOSITION HAVING ENHANCED MICELLE STABILITY, AND PHARMACEUTICAL COMPOSITION COMPRISING SAME

(71) Applicant: SAMYANG HOLDINGS CORPORATION, Seoul (KR)

(72) Inventors: Bong Oh Kim, Daejeon (KR); Kyu Jin Kyung, Yangju-si (KR); Sa Won Lee, Seongnam-si (KR)

(73) Assignee: SAMYANG HOLDINGS CORPORATION, Seoul (KR)

( * ) Notice: Subject to any disclaimer, the term of this patent is extended or adjusted under 35 U.S.C. 154(b) by 0 days.

(21) Appl. No.: 16/469,392

(22) PCT Filed: Nov. 29, 2017

(86) PCT No.: PCT/KR2017/013863
§ 371 (c)(1),
(2) Date: Jun. 13, 2019

(87) PCT Pub. No.: WO2018/110870
PCT Pub. Date: Jun. 21, 2018

(65) Prior Publication Data
US 2019/0328880 A1    Oct. 31, 2019

(30) Foreign Application Priority Data
Dec. 14, 2016    (KR) .................. 10-2016-0170266

(51) Int. Cl.
*A61K 47/10*     (2017.01)
*A61K 9/107*     (2006.01)
(Continued)

(52) U.S. Cl.
CPC ............ *A61K 47/10* (2013.01); *A61K 9/1075* (2013.01); *A61K 31/337* (2013.01); *A61K 47/32* (2013.01);
(Continued)

(58) Field of Classification Search
CPC ..................................................... A61K 47/10
See application file for complete search history.

(56) References Cited

U.S. PATENT DOCUMENTS

2003/0143184 A1    7/2003    Seo et al.
2003/0180363 A1    9/2003    Seo et al.
(Continued)

FOREIGN PATENT DOCUMENTS

CN    106995528 A    8/2017
JP    2000-511161 A    8/2000
(Continued)

OTHER PUBLICATIONS

International Search Report issued in PCT/KR2017/013863 (PCT/ISA/210), dated Mar. 29, 2018.
(Continued)

*Primary Examiner* — Benjamin J Packard
(74) *Attorney, Agent, or Firm* — Birch, Stewart, Kolasch & Birch, LLP

(57) ABSTRACT

The present invention relates to an amphiphilic block copolymer composition which provides enhanced stability to a micelle formed by an amphiphilic block copolymer in an aqueous phase.

9 Claims, 2 Drawing Sheets

(51) Int. Cl.
    *A61K 31/337*     (2006.01)
    *A61K 47/32*     (2006.01)
    *A61K 47/34*     (2017.01)
    *B01J 20/281*     (2006.01)
    *G01N 30/00*     (2006.01)

(52) U.S. Cl.
    CPC .............. *A61K 47/34* (2013.01); *G01N 30/48* (2013.01); *G01N 2030/486* (2013.01)

(56) References Cited

U.S. PATENT DOCUMENTS

| | | |
|---|---|---|
| 2004/0197408 A1 | 10/2004 | Gravett |
| 2005/0238618 A1 | 10/2005 | Huang |
| 2010/0280214 A1 | 11/2010 | Kim et al. |
| 2011/0268772 A1 | 11/2011 | Kim et al. |

FOREIGN PATENT DOCUMENTS

| | | |
|---|---|---|
| JP | 2012-513460 A | 6/2012 |
| KR | 10-2001-0104286 A | 11/2001 |
| KR | 10-2001-0105239 A | 11/2001 |
| KR | 10-2007-0036051 A | 4/2007 |
| KR | 10-2010-0097144 A | 9/2010 |
| KR | 10-2011-0077818 A | 7/2011 |
| WO | WO 97/45105 A1 | 12/1997 |

OTHER PUBLICATIONS

Du et al., "Study on the Micell of mPEG-PLA-paclitaxel Block Copolymer Conjugates," Journal of Shenyang Pharmaceutical University, vol. 25, No. 1. Jan. 2008, pp. 1-5, with an English abstract, only English Abstract considered.

Han et al., "Preparation of PLA-mPEG Block Copolymer Micelle and Their Surface Tension," Chinese Journal of Applied Chemistry, vol. 22, No. 4, Apr. 2005, pp. 403-406, with an English abstract, only English Abstract considered.

Extended European Search Report, dated Jun. 19, 2020, for European Application No. 17879714.8.

[Figure 1]
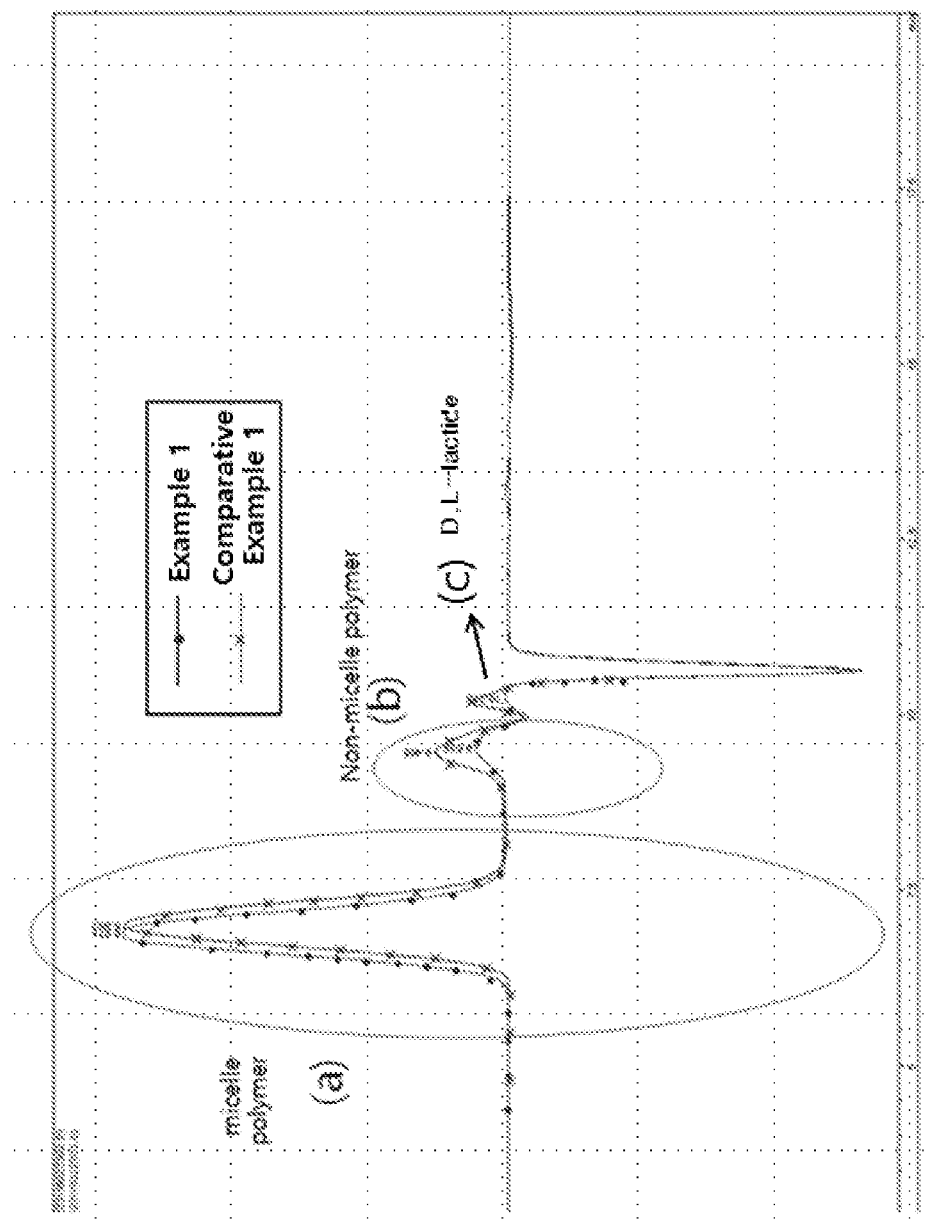

[Figure 2]
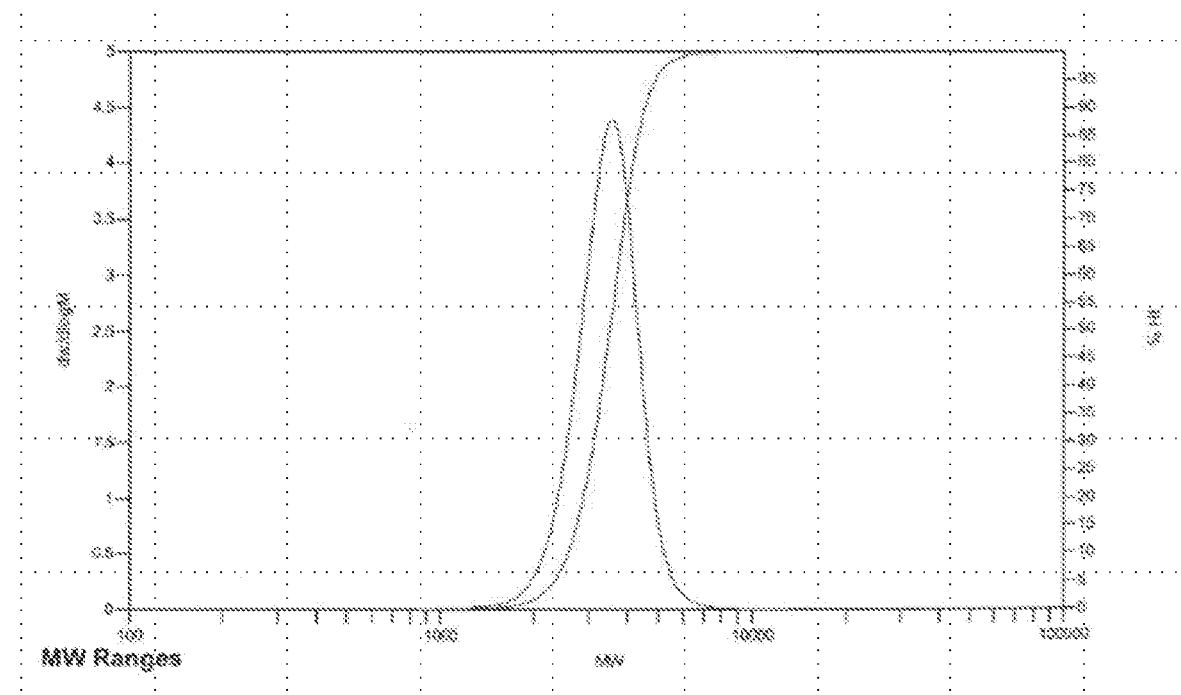

AMPHIPHILIC BLOCK COPOLYMER COMPOSITION HAVING ENHANCED MICELLE STABILITY, AND PHARMACEUTICAL COMPOSITION COMPRISING SAME

TECHNICAL FIELD

The present disclosure relates to an amphiphilic block copolymer composition which provides improved stability to a micelle prepared from the amphiphilic block copolymer in an aqueous solution, and more specifically, an amphiphilic block copolymer composition having increased micelle stability by removing non-micelle polymer and monomers, and a pharmaceutical composition comprising the amphiphilic block copolymer.

BACKGROUND ART

An amphiphilic block copolymer is composed of a hydrophilic polymer block and a hydrophobic polymer block. Since the hydrophilic polymer block directly contacts with blood proteins and cell membranes in vivo, biocompatible polyethylene glycol or monomethoxypolyethylene glycol, etc. has been used. The hydrophobic polymer block improves the affinity with hydrophobic drugs, and biodegradable polylactide, polyglycolide, poly(lactic-glycolide), polycaprolactone, polyamino acid, polyorthoester and the like have been used. Particularly, polylactide derivatives have excellent biocompatibility and are hydrolyzed in the body into harmless lactic acid, and thus they have been applied to drug carriers in various forms. The polylactide derivatives have various properties depending on their molecular weight and have been developed in the forms of microspheres, nanoparticles, polymeric gel, implant agent and the like.

In an amphiphilic block copolymer used as a drug carrier, the release rate of drug can be controlled by adjusting the composition ratio and each molecular weight, etc. of the hydrophilic and hydrophobic blocks. In order to control the release rate of drug accurately, the content of the amphiphilic block copolymer which is able to form micelles is important. If the non-micelle polymer is included in the final amphiphilic block copolymer, the molecular weight distribution is widened and the content of the amphiphilic block copolymer that does not form micelles is increased. This reduces the physical stability of the micelles which encapsulate the drug. In addition, when the drug is administered to the human body, the stability of the drug encapsulated in the micelles may be lowered and excessive release may occur.

There are various purification methods for increasing the purity of the amphiphilic block copolymer. A technique for purifying an amphiphilic block copolymer comprising polylactide derivative as a hydrophobic block by a solvent/non-solvent method has been known. In this method, the combination of methylene chloride/ether is used as the solvent/non-solvent combination for purification to remove D,L-lactide monomer. However, this method is not effective on the removal of non-micelle polymer since the solubility of the hydrophilic block (polyethylene glycol) to ether is low. The boiling point of the ether used as the non-solvent is very low, and thus said method has many problems in the application of the industrial process.

Another purification method is a method of removing monomers without using a solvent. In this method, after synthesizing an amphiphilic copolymer comprising polylactide derivative, unreacted lactide monomer is removed by a sublimation method under high temperature and vacuum conditions using its sublimating property. This method can be advantageously applied for industrialization. However, said method can only remove monomers. In addition, it is difficult to control the molecular weight as desired due to the thermal decomposition of the synthesized polymer under high temperature and vacuum conditions for a long time.

Korean Patent No. 10-1187487 discloses a process for preparing a high-purity amphiphilic block copolymer by dissolving a polymer using a hydrophilic solvent and a basic aqueous solution, followed by layer separation using a salting-out method in which sodium chloride is added. When layer separation occurs, impurities that have a significantly higher solubility in aqueous solution than the solubility in a hydrophilic solvent are removed. However, in case of the non-micelle polymer there is a problem in that the removal efficiency is reduced because of its high solubility in a hydrophilic solvent.

US Patent Publication No. 2005-0238618 discloses a method for purifying low molecular weight D,L-polylactic acid by a liquid/liquid phase separation method. In this method, a polymerized polymer is dissolved by heating in methanol or ethanol, and then stored at −78° C. for freezing to cause layer separation. The low molecular weight polylactic acid is dissolved in the organic solvent in the upper layer, and the high molecular weight polylactic acid is solidified in the lower layer. The lower layer is separated, and the solvent is distilled off to remove the monomers and oligomers to obtain a high-purity D,L-polylactic acid having a narrow molecular weight distribution. However, in the case of the amphiphilic block copolymer, since its solubility is significantly lowered at low temperatures, layer separation does not occur and thus there is a problem in removing the non-micelle polymer only.

Therefore, there is a need for a purification method capable of removing non-micelle polymer from an amphiphilic block copolymer comprising a hydrophobic polymer block of poly(α-hydroxy acid).

CONTENTS OF THE INVENTION

Problems to be Solved

One purpose of the present disclosure is to provide an amphiphilic block copolymer composition capable of forming micelles with improved stability due to a low content of non-micelle polymer, and a pharmaceutical composition comprising the same.

Another purpose of the present disclosure is to provide a method for effectively removing monomers as well as non-micelle polymers by a liquid/liquid phase separation method in purifying an amphiphilic block copolymer composition.

Yet another purpose of the present disclosure is to provide a use of an amphiphilic block copolymer composition for preparing a drug carrier.

Technical Means to Solve the Problems

One aspect of the present disclosure provides an amphiphilic block copolymer composition comprising a hydrophilic block (A) selected from the group consisting of polyethylene glycol or derivatives thereof, polyvinyl pyrrolidone, polyvinyl alcohol, polyacrylamide and combinations thereof; and a hydrophobic block (B) selected from the group consisting of polylactide, polyglycolide, polymandelic acid, polycaprolactone, polydioxan-2-one, polyamino acid, polyorthoester, polyanhydride, polycarbonate and combinations thereof, wherein the amphiphilic block copolymer composition satisfies the conditions of the following Equation 1:

Area of peak (a)/[Area of peak (a)+Area of peak (b)]×100≥85 [Equation 1]

wherein peak (a) is a peak indicated by a micelle polymer in size exclusion chromatogram, and peak (b) is a peak indicated by a non-micelle polymer in size exclusion chromatogram.

Another aspect of the present disclosure provides a pharmaceutical composition of polymeric micelle comprising the amphiphilic block copolymer composition and a poorly water-soluble drug.

Still another aspect of the present disclosure provides a method for purifying an amphiphilic block copolymer composition comprising (a) a step of dissolving an amphiphilic block copolymer composition comprising a hydrophilic block (A) and a hydrophobic block (B) in an organic solvent selected from the group consisting of ethanol, methanol, isopropyl alcohol and mixtures thereof at a temperature of 40° C. to 70° C. for 1 hour to 6 hours; and (b) a step of layer separation of the resulting solution from step (a) at a temperature of 15° C. to 35° C. for 1 hour to 6 hours.

Still another aspect of the present disclosure provides a use of the amphiphilic block copolymer composition for preparing a drug carrier.

Effects of the Invention

According to the present disclosure, an amphiphilic block copolymer composition, capable of forming micelles with improved stability due to a low content of non-micelle polymer, can be obtained. The amphiphilic block copolymer composition can be effectively purified without pyrolysis of the polymer, and thus it can be advantageously applied for industrialization. In addition, if a pharmaceutical composition is prepared using the amphiphilic block copolymer composition of the present disclosure, a pharmaceutical composition having excellent storage stability can be obtained because the physical stability of micelles is improved and the production of related substances is inhibited even in a storage stability test under severe condition.

BRIEF EXPLANATION OF THE DRAWINGS

FIG. 1 is the resulting chromatogram of size exclusion chromatogram (SEC) analysis conducted in Example 1 and Comparative Example 1 (unit of horizontal axis: min, unit of vertical axis: nRIU (nano refractive index unit). Peak (a) is a peak indicated by a micelle polymer which forms micelle, peak (b) is a peak indicated by an amphiphilic block copolymer which cannot form micelle and be in a soluble form (a non-micelle polymer), and peak (c) is a peak indicated by D,L-lactide which is a monomer. The content of micelle polymer in the amphiphilic block copolymer composition is represented by the ratio of areas of the peaks (a), (b) and (c), and satisfies the following Equation 1, and preferably satisfies the following Equations 1 and 2:

Area of peak (a)/[Area of peak (a)+Area of peak (b)]×100≥85 [Equation 1]

Area of peak (a)/[Area of peak (a)+Area of peak (b)+Area of peak (c)]×100≥85). [Equation 2]

FIG. 2 is the resulting chromatogram of gas permeation chromatography (GPC) analysis conducted in Example 1.

BEST MODE FOR CARRYING OUT THE INVENTION

The present disclosure is explained in more detail below.

In this specification, "micelle polymer" means an amphiphilic block copolymer which forms micelle in aqueous solution, and "non-micelle polymer>>" means an amphiphilic block copolymer which cannot form micelle and be in a soluble form.

According to one embodiment of the present disclosure, the amphiphilic block copolymer may be an A-B type diblock copolymer consisting of a hydrophilic block (A) and a hydrophobic block (B), or a B-A-B type triblock copolymer.

According to one embodiment of the present disclosure, the amphiphilic block copolymer may comprise the hydrophilic block in an amount of 20 to 95% by weight, and more specifically 40 to 95% by weight, based on the total of 100% by weight of the copolymer. In addition, the amphiphilic block copolymer may comprise the hydrophobic block in an amount of 5 to 80% by weight, and more specifically 5 to 60% by weight, based on the total of 100% by weight of the copolymer.

According to one embodiment of the present disclosure, the amphiphilic block copolymer may have a number average molecular weight of 1,000 to 50,000 Daltons, and more specifically 1,500 to 20,000 Daltons.

According to one embodiment of the present disclosure, the hydrophilic block may be a biocompatible polymer. Specifically, it may comprise one selected from the group consisting of polyethylene glycol or derivatives thereof, polyvinylpyrrolidone, polyvinyl alcohol, polyacrylamide and combinations thereof, and more specifically, it may comprise one selected from the group consisting of polyethylene glycol, monomethoxypolyethylene glycol and combinations thereof. The hydrophilic block may have a number average molecular weight of 200 to 20,000 Daltons, and more specifically 200 to 10,000 Daltons.

According to one embodiment of the present disclosure, the hydrophobic block may be a biodegradable polymer and a polymer of monomers derived from alpha (α)-hydroxy acid. Specifically, it may comprise one selected from the group consisting of polylactide, polyglycolide, poly(lactic-glycolide), polymandelic acid, polycaprolactone, polydioxan-2-one, polyamino acid, polyorthoester, polyanhydride, polycarbonate and combinations thereof, and more specifically, it may comprise one selected from the group consisting of polylactide, polyglycolide, poly(lactic-glycolide) and combinations thereof. The hydrophobic block may have a number average molecular weight of 200 to 20,000 Daltons, and more specifically 200 to 10,000 Daltons.

According to one embodiment of the present disclosure, an amphiphilic block copolymer comprising a hydrophobic polymer block of poly(alpha (α)-hydroxy acid) may be synthesized by a known ring-opening polymerization method using a hydrophilic polymer having hydroxyl group as an initiator, and a lactone monomer of alpha (α)-hydroxy acid. For example, L-lactide or D,L-lactide may be polymerized by ring opening with hydrophilic polyethylene glycol or monomethoxypolyethylene glycol having hydroxyl group as an initiator. Synthesis of diblock or triblock copolymer is possible according to the number of hydroxyl group existing in the hydrophilic block, which is the initiator. In the ring-opening polymerization, an organometallic catalyst such as tin oxide, lead oxide, tin octoate, antimony octoate, etc. may be used, and tin octoate having biocompatibility is preferably used in preparing polymer for medical use.

The amphiphilic block copolymer composition of the present disclosure satisfies the conditions of the following Equation 1, preferably satisfies the conditions of the following Equation 1a, and more preferably satisfies the conditions of the following Equation 1b.

$$\text{Area of peak } (a)/[\text{Area of peak } (a)+\text{Area of peak } (b)]\times 100 \geq 85 \quad \text{[Equation 1]}$$

$$\text{Area of peak } (a)/[\text{Area of peak } (a)+\text{Area of peak } (b)]\times 100 \geq 90 \quad \text{[Equation 1a]}$$

$$\text{Area of peak } (a)/[\text{Area of peak } (a)+\text{Area of peak } (b)]\times 100 \geq 95 \quad \text{[Equation 1b]}$$

In one embodiment, along with satisfying the conditions of Equation 1, the amphiphilic block copolymer composition of the present disclosure satisfies the conditions of the following Equation 2, preferably satisfies the conditions of the following Equation 2a, and more preferably satisfies the conditions of the following Equation 2b $$\text{Area of peak } (a)/[\text{Area of peak } (a)+\text{Area of peak } (b)+\text{Area of peak } (c)]\times 100 \geq 85 \quad \text{[Equation 2]}$$

$$\text{Area of peak } (a)/[\text{Area of peak } (a)+\text{Area of peak } (b)+\text{Area of peak } (c)]\times 100 \geq 90 \quad \text{[Equation 2a]}$$

$$\text{Area of peak } (a)/[\text{Area of peak } (a)+\text{Area of peak } (b)+\text{Area of peak } (c)]\times 100 \geq 95 \quad \text{[Equation 2b]}$$

In the above equations, peak (a) is a peak indicated by a micelle polymer in size exclusion chromatogram, peak (b) is a peak indicated by a non-micelle polymer in size exclusion chromatogram, and peak (c) is a peak indicated by a monomer.

A pharmaceutical composition, for example a pharmaceutical composition of polymeric micelle, can be prepared by using the amphiphilic block copolymer composition of the present disclosure satisfying the conditions of the above Equation 1 as a polymeric carrier of a drug (i.e., a drug carrier).

A pharmaceutical composition according to an example of the present disclosure may comprise a poorly water-soluble drug as an active ingredient. The poorly water-soluble drug may be selected from drugs having a solubility in water (25° C.) of 100 mg/mL or less. In addition, it can be selected from antineoplastic agents, antifungal agents, immunosuppressants, analgesics, anti-inflammatory agents, antiviral agents, anxiolytic sedatives, contrasting agents, corticosteroids, diagnostic agents, diagnostic imaging agents, diuretics, prostaglandins, radiopharmaceuticals, sex hormones including steroids and combinations thereof, but it is not limited thereto.

In one embodiment, the poorly water-soluble drug may be selected from antineoplastic agents, and specifically, it may be a taxane antineoplastic agent. For example, the taxane antineoplastic agents may be one or more selected from the group consisting of paclitaxel, docetaxel, 7-epipaclitaxel, t-acetylpaclitaxel, 10-desacetylpaclitaxel, 10-desacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel and cabazitaxel, and more specifically, it may be paclitaxel, docetaxel or a combination thereof.

In the method for preparing the pharmaceutical composition of the present disclosure, a conventional method for forming polymeric micelles can be used. In an example, the method for preparing the pharmaceutical composition of the present disclosure may comprise (a) a step of dissolving a poorly water-soluble drug and the amphiphilic block copolymer composition in an organic solvent; and (b) a step of adding an aqueous solvent to the solution obtained from step (a) to form polymeric micelles.

In the method for preparing the pharmaceutical composition of the present disclosure, as the organic solvent, a water-miscible organic solvent, for example, one selected from the group consisting of alcohol, acetone, tetrahydrofuran, acetic acid, acetonitrile, dioxane and combinations thereof can be used, but it is not limited thereto. In addition, as the aqueous solvent, one selected from the group consisting of conventional water, distilled water, distilled water for injection, saline, 5% glucose, buffer and combinations thereof can be used, but it is not limited thereto.

The method for preparing the pharmaceutical composition of the present disclosure may further comprise a step of removing the organic solvent after step (a).

The pharmaceutical composition prepared according to the method of the present disclosure may comprise the poorly water-soluble drug in an amount of 0.1 to 50 parts by weight, and more specifically 0.5 to 30 parts by weight, based on 100 parts by weight of the amphiphilic block copolymer composition. If the amount of the poorly water-soluble drug is too small as compared with that of the amphiphilic block copolymer, the weight ratio of the amphiphilic copolymer used per drug is high and thus the time for reconstitution before administration may increase. On the other hand, if the amount of the poorly water-soluble drug is too large, there may be a problem of rapid precipitation of the poorly water-soluble drug.

The present disclosure also provides a method for purifying an amphiphilic block copolymer composition comprising (a) a step of dissolving an amphiphilic block copolymer composition comprising a hydrophilic block (A) and a hydrophobic block (B) in an organic solvent selected from the group consisting of ethanol, methanol, isopropyl alcohol and mixtures thereof at a temperature of 40° C. to 70° C. for 1 hour to 6 hours; and (b) a step of layer separation of the resulting solution from step (a) at a temperature of 15° C. to 35° C. for 1 hour to 6 hours.

In one embodiment, in step (a) the temperature for dissolving the amphiphilic block copolymer composition in the organic solvent may be preferably 40° C. to 60° C., and more preferably 45° C. to 55° C., and the dissolving time may be preferably 1 hour to 4 hours, and more preferably 2 hours to 3 hours. In addition, in step (b) the temperature for layer separation may be preferably 1 hour to 4 hours, and more preferably 2 hours to 3 hours. If the layer separation is performed under the above conditions, impurities such as a monomer and a catalyst can be removed and non-micelle polymer can be efficiently removed.

In one embodiment, the organic solvent used in step (a) may be in an amount of preferably 2 ml/g to 8 ml/g, and more preferably 4 ml/g to 6 ml/g, based on the weight of the amphiphilic block copolymer composition. As the amount of the organic solvent used is higher than that of the polymer, the purification efficiency tends to increase and the yield tends to decrease. In addition, ethanol can be preferably used as the organic solvent. Ethanol is the least toxic solvent available in the manufacture of medicine.

Furthermore, in one embodiment, the purification method of the present disclosure may further comprise a step of removing remaining organic solvent from the result of step (b).

In one embodiment, in the amphiphilic block copolymer composition of the present disclosure, the content of the amphiphilic block copolymer which cannot form micelles in aqueous solution (i.e., non-micelle polymer) is 10% or less (when analyzed by SEC).

MODE FOR CARRYING OUT THE INVENTION

The present disclosure is explained in more detail by the following examples. However, these examples seek to illustrate the present invention only, and the scope of the present invention is not limited by the examples in any manner.

EXAMPLES

Preparation Example 1

Synthesis of Diblock Copolymer Consisting of monomethoxypolyethylene glycol and D,L-lactide (mPEG-PDLLA)

150 g of monomethoxypolyethylene glycol (mPEG, number average molecular weight=2,000) was fed into a 500-ml round-bottom flask equipped with an agitator and agitated at 120° C. under vacuum condition for 2 hours to remove moisture. 0.15 g of tin octoate $(Sn(Oct)_2)$ dissolved in 200 µl of toluene was added into the reaction flask, and further agitated under vacuum condition for 1 hour to distill and remove toluene. 150 g of D,L-lactide was then added and agitated under nitrogen atmosphere for dissolution. After D,L-lactide was dissolved completely, the reactor was tightly sealed and the polymerization reaction was conducted at 120° C. for 10 hours.

Example 1

Purification of Diblock Copolymer (mPEG-PDLLA) by Layer Separation Method Using Ethanol 20 g of mPEG-PDLLA obtained in Preparation Example 1 was fed into a one-necked flask, 120 ml of ethanol was added thereto, and dissolved at 50° C. for 2 hours with agitation. Polymer solution was moved to a separatory funnel, and layer separation occurs at 25° C. for 2 hours. After the layer separation was completed, polymer solution in the lower layer was moved to one-necked flask. Remaining ethanol in the polymer solution was removed by vacuum distillation using a vacuum distiller.

The sample of the purified copolymer was obtained and analyzed with $^1$H-NMR, and the content of lactide and the molecular weight was calculated by obtaining relative intensities of appropriate peaks with reference to —OCH$_3$ which is the terminal group of monomethoxypolyethylene glycol. The purified copolymer was further analyzed by GPC and SEC under the conditions below. The results are shown in the following Table 1.

[SEC Analysis Conditions]
mPEG-PDLLA was dissolved in water to make a concentration of 0.5% and then analyzed.
(1) SEC column: Shodex, OHpak SB-804 HQ (8.0×300 mm)
(2) Mobile phase: Phosphate buffered saline solution 100%
(3) Flow rate: 1 mL/min
(4) Injection amount: 50 µL
(5) Detector: RID
(6) Temperature: 25° C.

[GPC Analysis Conditions]
6.0 mg of mPEG-PDLLA was weighed, and 4 ml of HPLC grade chloroform was added thereto for dissolving the polymer. Polyethylene glycol (610, 1010, 1480, 4040, 7830, 16100, 21300 g/mol) was used as a reference material.
(1) GPC column: Plgel 5 µm Mixed-C Analytical column (Agilent)
(2) Mobile phase: HPLC grade Chloroform
(3) Flow rate: 1 mL/min
(4) Injection amount: 100 µL
(5) Detector: RID
(6) Temperature: 35° C.

Comparative Example 1

Purification of Diblock Copolymer (mPEG-PDLLA) by Sublimation Method 30 g of mPEG-PDLLA obtained in Preparation Example 1 was fed into a one-necked flask and dissolved at 120° C. Under agitation with a magnetic bar, the reactor was connected to a vacuum pump and lactide was removed under a pressure of 1 torr or less by a sublimation method for 7 hours. The obtained copolymer was analyzed as in Example 1, and the result is shown in the following Table 1.

TABLE 1

|  |  | Example 1 | Comparative Example 1 |
|---|---|---|---|
| Molecular weight (Mn by $^1$H-NMR) |  | 4030 | 3770 |
| Content of lactide (wt % by $^1$H-NMR) |  | 0.12 | 1.83 |
| Ratio of micelle/non-micelle polymer (Area % by SEC) |  | 95.7/4.3 | 82.2/17.8 |
| GPC analysis | Number average molecular weight (Mn) | 3300 | 3160 |
|  | Weight average molecular weight (Mw) | 3530 | 3410 |
|  | Polydispersity index (PDI) | 1.07 | 1.08 |

In view of the results of Table 1, it can be seen from the SEC analysis that the removal of monomer is better and non-micelle polymer was further removed in the purification by the layer separation method using ethanol than in the purification by the sublimation method. [While the area of lactide (Area by SEC) was 0 in Example 1, a peak was observed in Comparative Example 1 ((c) of FIG. 1).] In addition, from the GPC analysis result it was confirmed that the average molecular weight of the amphiphilic block copolymer was increased, and PDI decreases and the molecular weight distribution was further narrowed.

Example 2

Preparation of Polymeric Micelle Composition Containing Paclitaxel by using the Polymer Purified by the Layer Separation Method using Ethanol 5 g of mPEG-PDLLA obtained in Example 1 and 1 g of paclitaxel were weighed, and 4 ml of ethanol was added thereto and agitated at 60° C. until the mixture was completely dissolved to form a clear solution. Ethanol was then removed by distillation under reduced pressure using a rotary evaporator equipped with a round-bottom flask at 60° C. for 3 hours. The temperature was then lowered to 50° C., and 140 ml of distilled water at room temperature was added and reacted until the solution became clear in blue color to form polymeric micelles. As a lyophilization aid, 2.5 g of anhydrous lactose was added thereto and dissolved completely, filtered using a filter with a pore size of 200 nm, and freeze-dried to obtain a polymeric micelle composition containing paclitaxel as a powder form.

Comparative Example 2

Preparation of Polymeric Micelle Composition Containing Paclitaxel by using the Polymer Purified by Sublimation Method Except that the mPEG-PDLLA obtained in Comparative Example 1 was used, a polymeric micelle composition containing paclitaxel was prepared by the same method as in Example 2.

Example 3

Preparation of Polymeric Micelle Composition Containing Docetaxel by using the Polymer Purified by the Layer Separation Method using Ethanol 19 g of mPEG-PDLLA obtained in Example 1 and 1 g of docetaxel were weighed, and 7 ml of ethanol was added thereto and agitated at 25° C. until the mixture was completely dissolved to form a clear solution. Ethanol was then removed by distillation under reduced pressure using a rotary evaporator equipped with a round-bottom flask at 25° C. for 3 hours. 225 ml of distilled water at room temperature was then added and reacted until the solution became clear in blue color to form polymeric micelles. As a lyophilization aid, 5.0 g of anhydrous lactose was added thereto and dissolved completely, filtered using a filter with a pore size of 200 nm, and freeze-dried to obtain a polymeric micelle composition containing docetaxel as a powder form.

Comparative Example 3

Preparation of Polymeric Micelle Composition Containing Docetaxel by using the Polymer Purified by Sublimation Method Except that the mPEG-PDLLA obtained in Comparative Example 1 was used, a polymeric micelle composition containing docetaxel was prepared by the same method as in Example 3.

Experimental Example 1

Comparative Test of Storage Stability of Polymeric Micelle Containing Paclitaxel at Severe Condition The polymeric micelle compositions containing paclitaxel (Example 2 and Comparative Example 2) were kept in an oven at 60° C. for 2 weeks or 4 weeks, and the test solutions were prepared by dissolving the polymeric micelle compositions in 80% acetonitrile aqueous solution and diluting to 600 ppm concentration of paclitaxel. The prepared test solutions were then analyzed with HPLC under the following conditions to compare the amounts of the related substances, and the change in the amount of the related substances (%) depending on the severe test time is shown in the following Table 2.

The particle diameter of the micelles was measured by an average diameter using a Dynamic Scattering Instrument. The measurement results are shown in Table 2 below.

[HPLC Conditions]
Column: Diameter 2.7 μm, poroshell 120PFP (4.6×150 mm, 2.7 μm) (Agilent column)
Mobile Phase

| Time (min) | Water:Acetonitrile |
|---|---|
| 0~25 | 65:35 → 45:55 |
| 25~28 | 45:55 |
| 28~30 | 45:55 → 65:35 |
| 30~35 | 65:35 |

Detector: UV absorption spectrophotometer (227 nm)
Flow rate: 0.6 ml/min
Amount of each related substance (%)=100(Ri/Ru)
Ri: Area of each related substance detected in test solution analysis
Ru: Sum of all peak areas detected in test solution analysis

TABLE 2

| Analysis items | | 0 | 2 weeks | 4 weeks |
|---|---|---|---|---|
| Related substances (%) | Example 2 | N.D. | 0.087 | 0.39 |
| | Comparative Example 2 | N.D. | 0.63 | 1.92 |
| Particle diameter (nm) | Example 2 | 21.3 | 25.7 | 23.2 |
| | Comparative Example 2 | 21.2 | 22.3 | 21.4 |

N.D.: Not detected

The results of Table 2 show that the generation of the related substances was remarkably suppressed in the drug-containing micelle using the polymer purified by the ethanol layer separation method. It is expected to improve storage stability in case of product development.

Experimental Example 2

Comparative Test of Storage Stability of Polymeric Micelle Containing Docetaxel at Severe Condition The polymeric micelle compositions containing docetaxel (Example 3 and Comparative Example 3) were kept in an oven at 40° C. for 1 week, 2 weeks or 4 weeks, and the test solutions were prepared by dissolving 20 mg of the polymeric micelle compositions in 10 ml water and diluting with mobile phase so that the total volume of the test solution is 50 ml. The prepared test solutions were then analyzed with HPLC under the following conditions to compare the amounts of the related substances. The change in the amount of the related substances (%) depending on the severe test time is shown in the following Table 3.

The particle diameter of the micelles was measured by an average diameter using a Dynamic Scattering Instrument. The measurement results are shown in Table 3 below.

[HPLC Conditions]
Column: Lichrospher 100 RP-18, 250×4.0 mm (5 μm) or a similar column
Mobile phase: acetonitrile: methanol: water mixture (26:32:42)
Flow rate: 1.5 ml/min
Injection amount: 20 μl
Detector: UV absorption spectrophotometer (232 nm)
Column temperature: 20° C.
Amount of each related substance (%)=100(Ri/Ru)
Ri: Area of each related substance detected in test solution analysis
Ru: Sum of all peak areas detected in test solution analysis

TABLE 3

| Analysis items | | 0 | 1 week | 2 weeks | 4 weeks |
|---|---|---|---|---|---|
| Related substances (%) | Example 3 | N.D. | N.D. | N.D. | 0.25 |
| | Comparative Example 3 | 0.43 | 0.86 | 1.14 | 1.47 |
| Particle diameter (nm) | Example 3 | 19.8 | 22.4 | 40.0 | 339 |
| | Comparative Example 3 | 19.7 | PPT | PPT | PPT |

N.D.: Not detected
PPT: Stability of micelles was reduced and precipitation of the drug was observed The results of Table 3 show that the generation of the related substances was remarkably suppressed in the drug-containing micelle using the polymer purified by the ethanol layer separation method. It was confirmed that stability of the micelle is increased and the drug is stably contained in the micelle for a long period of time. In the case of using the polymer purified by the sublimation method, however, precipitation of drug was observed during the experimental period.

The invention claimed is:

1. A method for purifying an amphiphilic block copolymer composition, comprising:
   (a) a step of dissolving an amphiphilic block copolymer composition comprising a hydrophilic block (A) and a hydrophobic block (B) in an organic solvent selected from the group consisting of ethanol, methanol, isopropyl alcohol and mixtures thereof at a temperature of 40° C. to 70° C. for 1 hour to 6 hours; and
   (b) a step of layer separation of the resulting solution from step (a) at a temperature of 15° C. to 35° C. for 1 hour to 6 hours,
   wherein the amphiphilic block copolymer composition satisfies the conditions of the following Equation 1:

$$\text{Area of peak }(a)/[\text{Area of peak }(a)+\text{Area of peak }(b)]\times 100\geq 85 \quad \text{[Equation 1]}$$

wherein peak (a) is a peak indicated by a micelle polymer in size exclusion chromatogram, and
   peak (b) is a peak indicated by a non-micelle polymer in size exclusion chromatogram.

2. The method for purifying an amphiphilic block copolymer composition according to claim 1, wherein the organic solvent used in step (a) is in an amount of 2 ml/g to 8 ml/g based on the weight of the amphiphilic block copolymer composition.

3. The method for purifying an amphiphilic block copolymer composition according to claim 1, wherein the organic solvent used in step (a) is ethanol.

4. The method for purifying an amphiphilic block copolymer composition according to claim 1, further comprising a step of removing remaining organic solvent from the result of step (b).

5. The method for purifying an amphiphilic block copolymer composition according to claim 1, wherein the amphiphilic block copolymer composition satisfies the conditions of the following Equation 1a:

$$\text{Area of peak }(a)/[\text{Area of peak }(a)+\text{Area of peak }(b)]\times 100\geq 90 \quad \text{[Equation 1a]}$$

wherein peak (a) is a peak indicated by a micelle polymer in size exclusion chromatogram, and
   peak (b) is a peak indicated by a non-micelle polymer in size exclusion chromatogram.

6. The method for purifying an amphiphilic block copolymer composition according to claim 1, wherein the amphiphilic block copolymer composition satisfies the conditions of the following Equation 1b:

$$\text{Area of peak }(a)/[\text{Area of peak }(a)+\text{Area of peak }(b)]\times 100\geq 95 \quad \text{[Equation 1b]}$$

wherein peak (a) is a peak indicated by a micelle polymer in size exclusion chromatogram, and
   peak (b) is a peak indicated by a non-micelle polymer in size exclusion chromatogram.

7. The method for purifying an amphiphilic block copolymer composition according to claim 1, wherein the amphiphilic block copolymer composition satisfies the conditions of the following Equation 2:

$$\text{Area of peak }(a)/[\text{Area of peak }(a)+\text{Area of peak }(b)+\text{Area of peak }(c)]\times 100\geq 85 \quad \text{[Equation 2]}$$

wherein peak (a) is a peak indicated by a micelle polymer in size exclusion chromatogram,
   peak (b) is a peak indicated by a non-micelle polymer in size exclusion chromatogram, and
   peak (c) is a peak indicated by a monomer in size exclusion chromatogram.

8. The method for purifying an amphiphilic block copolymer composition according to claim 1, wherein the amphiphilic block copolymer composition satisfies the conditions of the following Equation 2a:

$$\text{Area of peak }(a)/[\text{Area of peak }(a)+\text{Area of peak }(b)+\text{Area of peak }(c)]\times 100\geq 90 \quad \text{[Equation 2a]}$$

wherein peak (a) is a peak indicated by a micelle polymer in size exclusion chromatogram,
   peak (b) is a peak indicated by a non-micelle polymer in size exclusion chromatogram, and
   peak (c) is a peak indicated by a monomer in size exclusion chromatogram.

9. The method for purifying an amphiphilic block copolymer composition according to claim 1, wherein the amphiphilic block copolymer composition satisfies the conditions of the following Equation 2b:

$$\text{Area of peak }(a)/[\text{Area of peak }(a)+\text{Area of peak }(b)+\text{Area of peak }(c)]\times 100\geq 95 \quad \text{[Equation 2b]}$$

wherein peak (a) is a peak indicated by a micelle polymer in size exclusion chromatogram,
   peak (b) is a peak indicated by a non-micelle polymer in size exclusion chromatogram, and
   peak (c) is a peak indicated by a monomer in size exclusion chromatogram.

\* \* \* \* \*